United States Patent [19]

Zones et al.

[11] Patent Number: 5,691,463
[45] Date of Patent: *Nov. 25, 1997

[54] ALKYLATION PROCESS USING ZEOLITE SSZ-25

[75] Inventors: Stacey I. Zones, San Francisco; Dennis L. Holtermann, Crockett; Robert A. Innes, San Rafael; Theresa A. Pecoraro, Blackhawk; Donald S. Santilli, Larkspur; James N. Ziemer, Hercules, all of Calif.

[73] Assignee: Chevron U.S.A. Inc., San Francisco, Calif.

[*] Notice: The term of this patent shall not extend beyond the expiration date of Pat. No. 5,149,894.

[21] Appl. No.: 682,949

[22] Filed: Jul. 16, 1996

Related U.S. Application Data

[60] Continuation of Ser. No. 486,478, Jun. 7, 1995, Pat. No. 5,591,322, which is a division of Ser. No. 897,222, Jun. 11, 1992, Pat. No. 5,421,992, which is a continuation of Ser. No. 788,656, Nov. 6, 1991, Pat. No. 5,202,014, which is a continuation of Ser. No. 333,666, Apr. 5, 1989, abandoned, which is a division of Ser. No. 14,958, Feb. 17, 1987, Pat. No. 4,826,667, which is a continuation-in-part of Ser. No. 823,698, Jan. 29, 1986, abandoned.

[51] Int. Cl.$^6$ ......................................................... C07C 2/66
[52] U.S. Cl. ........................................... 585/467; 423/326
[58] Field of Search .............................. 585/467; 423/326

[56] References Cited

U.S. PATENT DOCUMENTS

| | | | |
|---|---|---|---|
| 4,439,409 | 3/1984 | Puppe et al. | 423/324 |
| 4,544,538 | 10/1985 | Zones | 423/432.6 |
| 4,589,976 | 5/1986 | Zones | 208/111 |
| 4,665,110 | 5/1987 | Zones | 423/277 |
| 4,826,667 | 5/1989 | Zones et al. | 423/277 |
| 4,891,458 | 1/1990 | Innes et al. | 585/323 |
| 4,950,823 | 8/1990 | Harandi et al. | 585/322 |
| 4,954,325 | 9/1990 | Rubin | 423/328 |
| 4,992,606 | 2/1991 | Kushnerick et al. | 585/457 |
| 5,149,894 | 9/1992 | Holtermann et al. | 585/467 |
| 5,202,014 | 4/1993 | Zones et al. | 585/640 |
| 5,273,645 | 12/1993 | Clark et al. | 208/87 |
| 5,461,180 | 10/1995 | Andeh et al. | 585/467 |

*Primary Examiner*—Helane E. Myers
*Attorney, Agent, or Firm*—Burns, Doane, Swecker & Mathis

[57] ABSTRACT

A crystalline zeolite SSZ-25 is prepared using an adamantane quaternary ammonium ion as a template.

4 Claims, No Drawings

ALKYLATION PROCESS USING ZEOLITE SSZ-25

CROSS-REFERENCE TO RELATED APPLICATION

This application is a continuation, of application Ser. No. 08/486,478, filed Jun. 7, 1995 now U.S. Pat. No. 5,591,322, which is a divisional of application Ser. No. 07/897,222, filed Jun. 11, 1992 (now U.S. Pat. No. 5,421,992); which is a continuation of application Ser. No. 07/788,656, filed Nov. 6, 1991 (now U.S. Pat. No. 5,202,014); which is a continuation of application Ser. No. 07/333,666, filed Apr. 5, 1989, (abandoned); which is a divisional of application Ser. No. 07/014,958, filed Feb. 17, 1987 (now U.S. Pat. No. 4,826,667); which is a continuation-in-part of application Ser. No. 823,698, filed Jan. 29, 1986 (abandoned).

BACKGROUND OF THE INVENTION

Natural and synthetic zeolitic crystalline aluminosilicates are useful as catalysts and adsorbents. These aluminosilicates have distinct crystal structures which are demonstrated by X-ray diffraction. The crystal structure defines cavities and pores which are characteristic of the different species. The adsorptive and catalytic properties of each crystalline aluminosilicate are determined in part by the dimensions of its pores and cavities. Thus, the utility of a particular zeolite in a particular application depends at least partly on its crystal structure.

Because of their unique molecular sieving characteristics, as well as their catalytic properties, crystalline aluminosilicates are especially useful in such applications as gas drying and separation and hydrocarbon conversion. Although many different crystalline aluminosilicates and silicates have been disclosed, there is a continuing need for new zeolites and silicates with desirable properties for gas separation and drying, hydrocarbon and chemical conversions, and other applications.

Crystalline aluminosilicates are usually prepared from aqueous reaction mixtures containing alkali or alkaline earth metal oxides, silica, and alumina. "Nitrogenous zeolites" have been prepared from reaction mixtures containing an organic templating agent, usually a nitrogen-containing organic cation. By varying the synthesis conditions and the composition of the reaction mixture, different zeolites can be formed using the same templating agent. Use of N,N,N-trimethyl cyclopentyl-ammonium iodide in the preparation of Zeolite SSZ-15 molecular sieve is disclosed in my co-pending application Ser. No. 437,709, filed on Oct. 29, 1982; use of 1-azoniaspiro [4.4] nonyl bromide and N,N,N-trimethyl neopentylammonium iodide in the preparation of a molecular sieve termed "Losod" is disclosed in Helv. Chim. Acta (1974); Vol. 57, page 1533 (W. Sieber and W. M. Meier); use of quinuclidinium compounds to prepare a zeolite termed "NU-3" is disclosed in European Patent Publication No. 40016; use of 1,4-di(1-azoniabicyclo [2.2.2.]octane) lower alkyl compounds in the preparation of Zeolite SSZ-16 molecular sieve is disclosed in U.S. Pat. No. 4,508,837; use of N,N,N-trialkyl-1-adamantamine in the preparation of Zeolite SSZ-13 molecular sieve is disclosed in U.S. Pat. No. 4,544,538.

SUMMARY OF THE INVENTION

I have prepared a family of crystalline aluminosilicate molecular sieves with unique properties, referred to herein as "Zeolite SSZ-25", or simply "SSZ-25", and have found a highly effective method for preparing SSZ-25.

SSZ-25 has a mole ratio of an oxide selected from silicon oxide, germanium oxide, and mixtures thereof to an oxide selected from aluminum oxide, gallium oxide, iron oxide, boron oxide and mixtures thereof in the range of 20 to 200, and having the X-ray diffraction lines of Table 1 below. The zeolite further has a composition, as synthesized and in the anhydrous state, in terms of mole ratios of oxides as follows: (0.1 to 2.0) (Q$_2$O:(0.1 to 2.0)M$_2$O:W$_2$O$_3$:(20 to 200)YO$_2$ wherein M is an alkali metal cation, W is selected from aluminum, gallium, iron, boron and mixtures thereof, Y is selected from silicon, germanium and mixtures thereof, and Q is an adamantane quaternary ammonium ion. SSZ-25 zeolites can have a YO$_2$:W$_2$O$_3$ mole ratio in the range of 20 to 200. As prepared, the silica:alumina mole ratio is typically in the range of 30:1 to about 100:1. Higher mole ratios can be obtained by treating the zeolite with chelating agents or acids to extract aluminum from the zeolite lattice. The silica:alumina mole ratio can also be increased by using silicon and carbon halides and other similar compounds. Preferably, SSZ-25 is an aluminosilicate wherein W is aluminum and Y is silicon.

My invention also involves a method for preparing SSZ-25 zeolites, comprising preparing an aqueous mixture containing sources of an adamantane quaternary ammonium ion, an oxide selected from aluminum oxide, gallium oxide, iron oxide, boron oxide and mixtures thereof, and an oxide selected from silicon oxide, germanium oxide, and mixtures thereof, and having a composition, in terms of mole ratios of oxides, falling within the following ranges: YO$_2$/W$_2$O$_3$, 20:1 to 200:1; and Q$_2$O/YO$_2$, 0.15:1 to 0.50:1; wherein Y is selected from silicon, germanium, and mixtures thereof, W is selected from aluminum, gallium, iron, boron and mixtures thereof, and Q is an adamantane quaternary ammonium ion; maintaining the mixture at a temperature of at least 100° C. until the crystals of said zeolite are formed; and recovering said crystals.

DETAILED DESCRIPTION OF THE INVENTION

SSZ-25 zeolites, as synthesized, have a crystalline structure whose X-ray powder diffraction pattern shows the following characteristic lines:

TABLE 1

| 2 Θ | d/n | I/I$_o$ |
|---|---|---|
| 3.05 | 29.0 | 20 |
| 6.42 | 13.77 | 100 |
| 7.18 | 12.31 | 100 |
| 7.88 | 11.22 | 47 |
| 9.62 | 9.19 | 53 |
| 15.75 | 5.63 | 27 |
| 19.37 | 4.58 | 47 |
| 22.57 | 3.94 | 50 |
| 23.05 | 3.86 | 30 |
| 26.03 | 3.42 | 73 |
| 26.85 | 3.32 | 33 |

Typical SSZ-25 aluminosilicate zeolites have the X-ray diffraction pattern of Tables 3–5.

The X-ray powder diffraction patterns were determined by standard techniques. The radiation was the K-alpha/doublet of copper and a scintillation counter spectrometer with a strip-chart pen recorder was used. The peak heights I and the positions, as a function of 2 Θ where Θ is the Bragg angle, were read from the spectrometer chart. From these measured values, the relative intensities, 100I/I$_o$, where I$_o$ is the intensity of the strongest line or peak, and d, the interplanar spacing in Angstroms corresponding to the recorded lines, can be calculated. The X-ray diffraction pattern of Table 1 is characteristic of SSZ-25 zeolites. The zeolite produced by exchanging the metal or other cations present in the zeolite with various other cations yields substantially the same diffraction pattern although there can be minor shifts in interplanar spacing and minor variations in relative intensity. Minor variations in the diffraction pattern can also result from variations in the organic compound used in the preparation and from variations in the silica-to-alumina mole ratio from sample to sample. Calcination can also cause minor shifts in the X-ray diffraction pattern. Notwithstanding these minor perturbations, the basic crystal lattice structure remains unchanged.

After calcination, the SSZ-25 zeolites have a crystalline structure whose X-ray powder diffraction pattern shows the following characteristic lines as indicated in Table 2 below:

TABLE 1

| 2 Θ | d/n | I/I$_o$ |
| --- | --- | --- |
| 3.4 | 25.5 | 17 |
| 7.19 | 12.30 | 100 |
| 8.04 | 11.00 | 55 |
| 10.06 | 8.78 | 63 |
| 14.35 | 6.17 | 40 |
| 16.06 | 5.51 | 17 |
| 22.77 | 3.90 | 38 |
| 23.80 | 3.74 | 20 |
| 26.08 | 3.417 | 65 |

The equilibrium sorption for water and n-hexane of SSZ-25 are listed in Table 3. These equilibrium sorption capacities were obtained on SSZ-25 samples prepared as described in Example 6.

TABLE 3

| Equilibrium Sorption Capacities of SSZ-25 |||
| --- | --- | --- |
| Amount of N-Hexane Sorbed (g/100 g activated sample) |||
| Zeolite Sample | P/Po = 0.20 ||
| A | 0.111 ||
| B | 0.121 ||
| C | 0.107 ||
| D | 0.106 ||
| Amount of H$_2$O Sorbed (g/100 g activated sample) |||
| Zeolite Sample | P/Po = 0.57 | P/Po = 0.20 |
| E | 0.126 | 0.063 |

Based on the measurements made with n-hexane, the equilibrium sorption capacity of SSZ-25 is greater than 10 wt. %.

These equilibrium sorption capacities were obtained using the method described in "Method for Rapid Determination of Adsorption Properties of Molecular Sieves", G. R. Landolt, Analytical Chemistry, Vol. 43, No. 4, 613–615. Based on this method, the zeolites were dried by heating them overnight at 650° F. in air and weighed. They were then loaded into ampoules, placed in the adsorption chamber, and evacuated to less than 1 micron. The adsorbate had been outgassed on the vacuum line and so only the vapor was in contact with the zeolite (no air). The samples were connected to the adsorbate, either water or n-hexane. The vapor pressure of the adsorbate was measured with a pressure transducer. Equilibrium sorption measurements were made at several P/Po values and the samples are at 22° C. (72° F.).

Equilibration was obtained in 3–6 hours. After equilibration, the samples were removed and weighed to determine the amount adsorbed. The vapor pressure of the adsorbate was controlled by immersing a glass vessel containing the latter in a temperature-controlled cryostat. P/Po may be varied over a wide range by adjusting the temperature of the adsorbate.

This approach differs from the approach used by Landolt; in that, we check if air has leaked into the adsorption chamber by monitoring the pressure during the adsorption. The pressure should agree with published vapor pressure/temperature data for that particular adsorbate at the temperature of the cryostat. If the pressure is higher, we know we have a leak which we have to correct. If air is present in the adsorption chamber, the rate of adsorption decreases and equilibrium may not be attained in the allotted time.

SSZ-25 zeolites can be suitably prepared from an aqueous solution containing sources of an alkali metal oxide, an adamantane quaternary ammonium ion, an oxide of aluminum, gallium, iron, boron or mixtures thereof, and an oxide of silicon or germanium, or mixture of the two. The reaction mixture should have a composition in terms of mole ratios falling within the following ranges:

|  | Broad | Preferred |
| --- | --- | --- |
| YO$_2$/W$_2$O$_3$ | 20–200 | 30–100 |
| OH$^-$/YO$_2$ | 0.10–1.0 | 0.20–0.40 |
| Q/YO$_2$ | 0.15–0.50 | 0.15–0.30 |
| M$^+$/YO$_2$ | 0.05–0.30 | 0.15–0.30 |
| H$_2$O/YO$_2$ | 20–300 | 35–60 |
| Q/Q + M$^+$ | 0.30–0.70 | 0.40–0.67 | wherein Q is an adamantane quaternary ammonium ion, Y is silicon, germanium or both, and W is aluminum, gallium, iron, boron or mixture thereof. M is an alkali metal, preferably sodium or potassium. The organic adamantane compound which acts as a source of the adamantane quaternary ammonium ion employed can provide hydroxide ion.

When using the adamantane quaternary ammonium hydroxide compound as a template, it has also been found that purer forms of SSZ-25 are prepared when there is an excess of the adamantane quaternary ammonium hydroxide compound present relative to the amount of alkali metal hydroxide and that when the OH$^-$/SiO$_2$ molar ratio is greater than 0.40, then M$^+$/SiO$_2$ molar ratio should be less than 0.20.

The adamantane quaternary ammonium ion component Q, of the crystallization mixture, is derived from an adamantane quaternary ammonium compound. Preferably, the adamantane quaternary ammonium ion is derived from a compound of the formula:

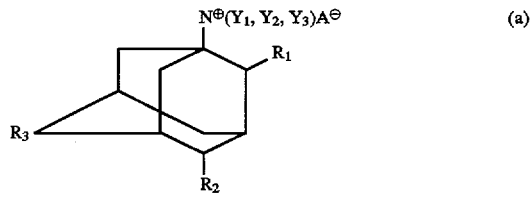

(a)

wherein each of Y$_1$, Y$_2$ and Y$_3$ independently is lower alkyl and most preferably methyl; A$^\ominus$ is an anion which is not detrimental to the formation of the zeolite; and each of R$_1$, R$_2$, and R$_3$ independently is hydrogen, or lower alkyl and most preferably hydrogen; and

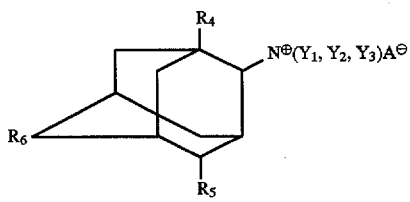

(b)

wherein each of $R_4$, $R_5$ and $R_6$ independently is hydrogen or lower alkyl; and most preferably hydrogen; each of $Y_1$, $Y_2$ and $Y_3$ independently is lower alkyl and most preferably methyl; and $A^\ominus$ is an anion which is not detrimental to the formation of the zeolite.

The adamantane quaternary ammonium compounds are prepared by methods known in the art.

By lower alkyl is meant alkyl of from about 1 to 5 carbon atoms.

$A^\ominus$ is an anion which is not detrimental to the formation of the zeolite. Representative of the anions include halide, e.g., fluoride, chloride, bromide and iodide, hydroxide, acetate, sulfate, carboxylate, etc. Hydroxide is the most preferred anion. It may be beneficial to ion-exchange, for example, the halide for hydroxide ion, thereby reducing or eliminating the alkali metal hydroxide quantity required.

The reaction mixture is prepared using standard zeolitic preparation techniques. Typical sources of aluminum oxide for the reaction mixture include aluminates, alumina, and aluminum compounds such as $AlCl_3$ and $Al_2(SO_4)_3$. Typical sources of silicon oxide include silicates, silica hydrogel, silicic acid, colloidal silica, tetraalkyl orthosilicates, and silica hydroxides. Gallium, iron, boron and germanium can be added in forms corresponding to their aluminum and silicon counterparts. Salts, particularly alkali metal halides such as sodium chloride, can be added to or formed in the reaction mixture. They are disclosed in the literature as aiding the crystallization of zeolites while preventing silica occlusion in the lattice.

The reaction mixture is maintained at an elevated temperature until the crystals of the zeolite are formed. The temperatures during the hydrothermal crystallization step are typically maintained from about 140° C. to about 200° C., preferably from about 160° C. to about 180° C., and most preferably from about 170° C. to about 180° C. The crystallization period is typically greater than 1 day and preferably from about 5 days to about 10 days.

The hydrothermal crystallization is conducted under pressure and usually in an autoclave so that the reaction mixture is subject to autogenous pressure. The reaction mixture can be stirred during crystallization.

Once the zeolite crystals have formed, the solid product is separated from the reaction mixture by standard mechanical separation techniques such as filtration. The crystals are water-washed and then dried, e.g., at 90° C. to 150° C. for from 8 to 24 hours, to obtain the as synthesized, SSZ-25 zeolite crystals. The drying step can be performed at atmospheric or subatmospheric pressures.

During the hydrothermal crystallization step, the SSZ-25 crystals can be allowed to nucleate spontaneously from the reaction mixture. The reaction mixture can also be seeded with SSZ-25 crystals both to direct, and accelerate the crystallization, as well as to minimize the formation of undesired aluminosilicate contaminants. If the reaction mixture is seeded with SSZ-25 crystals, the concentration of the organic compound can be greatly reduced or eliminated, but it is preferred to have some organic compound present, e.g., an alcohol.

The synthetic SSZ-25 zeolites can be used as synthesized or can be thermally treated (calcined). Usually, it is desirable to remove the alkali metal cation by ion exchange and replace it with hydrogen, ammonium, or any desired metal ion. The zeolite can be leached with chelating agents, e.g., EDTA or dilute acid solutions, to increase the silica:alumina mole ration. The zeolite can also be steamed; steaming helps stabilize the crystalline lattice to attack from acids. The zeolite can be used in intimate combination with hydrogenating components, such as tungsten, vanadium, molybdenum, rhenium, nickel, cobalt, chromium, manganese, or a noble metal, such as palladium or platinum, for those applications in which a hydrogenation-dehydrogenation function is desired. Typical replacing cations can include metal cations, e.g., rare earth, Group IIA and Group VIII metals, as well as their mixtures. Of the replacing metallic cations, cations of metals such as rare earth, Mn, Ca, Mg, Zn, Cd, Pt, Pd, Ni, Co, Ti, Al, Sn, Fe and Co are particularly preferred.

The hydrogen, ammonium, and metal components can be exchanged into the zeolite. The zeolite can also be impregnated with the metals, or the metals can be physically intimately admixed with the zeolite using standard methods known to the art. And, the metals can be occluded in the crystal lattice by having desired metals present as ions in the reaction mixture from which the SSZ-25 zeolite is prepared.

Typical ion exchange techniques involve contacting the synthetic zeolite with a solution containing a salt of the desired replacing cation or cations. Although a wide variety of salts can be employed, chlorides and other halides, nitrates, and sulfates are particularly preferred. Representative ion exchange techniques are disclosed in a wide variety of patents including U.S. Pat. Nos. 3,140,249; 3,140,251; and 3,140,253. Ion exchange can take place either before or after the zeolite is calcined.

Following contact with the salt solution of the desired replacing cation, the zeolite is typically washed with water and dried at temperatures ranging from 65° C. to about 315° C. After washing, the zeolite can be calcined in air or inert gas at temperatures ranging from about 200° C. to 820° C. for periods of time ranging from 1 to 48 hours, or more, to produce a catalytically active product especially useful in hydrocarbon conversion processes.

Regardless of the cations present in the synthesized form of the zeolite, the spatial arrangement of the atoms which form the basic crystal lattice of the zeolite remains essentially unchanged. The exchange of cations has little, if any, effect on the zeolite lattice structures.

The SSZ-25 aluminosilicate can be formed into a wide variety of physical shapes. Generally speaking, the zeolite can be in the form of a powder, a granule, or a molded product, such as extrudate having particle size sufficient to pass through a 2-mesh (Tyler) screen and be retained on a 400-mesh (Tyler) screen. In cases where the catalyst is molded, such as by extrusion with an organic binder, the aluminosilicate can be extruded before drying, or, dried or partially dried and then extruded. The zeolite can be composited with other materials resistant to the temperatures and other conditions employed in organic conversion processes. Such matrix materials include active and inactive materials and synthetic or naturally occurring zeolites as well as inorganic materials such as clays, silica and metal oxides. The latter may occur naturally or may be in the form of gelatinous precipitates, sols, or gels, including mixtures of silica and metal oxides. Use of an active material in conjunction with the synthetic zeolite, i.e., combined with it, tends to improve the conversion and selectivity of the catalyst in certain organic conversion processes. Inactive materials can suitably serve as diluents to control the amount of conversion in a given process so that products can be obtained economically without using other means for controlling the rate of reaction. Frequently, zeolite materials have been incorporated into naturally occurring clays, e.g., bentonite and kaolin. These materials, i.e., clays, oxides, etc., function, in part, as binders for the catalyst. It is desirable to provide a catalyst having good crush strength, because in petroleum refining the catalyst is often subjected to rough handling. This tends to break the catalyst down into powders which cause problems in processing.

Naturally occurring clays which can be composited with the synthetic zeolites of this invention include the montmorillonite and kaolin families, which families include the sub-bentonites and the kaolins commonly known as Dixie, McNamee, Georgia and Florida clays or others in which the main mineral constituent is halloysite, kaolinite, dickire, nacrite, or anauxite. Fibrous clays such as sepiolite and attapulgite can also be used as supports. Such clays can be used in the raw state as originally mined or can be initially subjected to calcination, acid treatment or chemical modification.

In addition to the foregoing materials, the SSZ-25 zeolites can be composited with porous matrix materials and mixtures of matrix materials such as silica, alumina, titania, magnesia, silica:alumina, silica-magnesia, silica-zirconia, silica-thoria, silica-beryllia, silica-titania, titania-zirconia as well as ternary compositions such as silica-alumina-thoria, silica-alumina-zirconia, silica-alumina-magnesia and silica-magnesia-zirconia. The matrix can be in the form of a cogel.

The SSZ-25 zeolites can also be composited with other zeolites such as synthetic and natural faujasites (e.g., X and Y), erionites, and mordenites. They can also be composited with purely synthetic zeolites such as those of the ZSM series. The combination of zeolites can also be composited in a porous inorganic matrix.

SSZ-25 zeolites are useful in hydrocarbon conversion reactions. Hydrocarbon conversion reactions are chemical and catalytic processes in which carbon containing compounds are changed to different carbon containing compounds. Examples of hydrocarbon conversion reactions include catalytic cracking, hydrocracking, and olefin and aromatics formation reactions. The catalysts are useful in other petroleum refining and hydrocarbon conversion reactions such as isomerizing n-paraffins and naphthenes, polymerizing and oligomerizing olefinic or acetylenic compounds such as isobutylene and butene-1, reforming, alkylating, isomerizing polyalkyl substituted aromatics (e.g., ortho xylene), and disproportionating aromatics (e.g., toluene) to provide mixtures of benzene, xylenes and higher methylbenzenes. The SSZ-25 catalysts have high selectivity, and under hydrocarbon conversion conditions can provide a high percentage of desired products relative to total products.

SSZ-25 zeolites can be used in processing hydrocarbonaceous feedstocks. Hydrocarbonaceous feedstocks contain carbon compounds and can be from many different sources, such as virgin petroleum fractions, recycle petroleum fractions, shale oil, liquefied coal, tar sand oil, and, in general, can be any carbon containing fluid susceptible to zeolitic catalytic reactions. Depending on the type of processing the hydrocarbonaceous feed is to undergo, the feed can contain metal or be free of metals, it can also have high or low nitrogen or sulfur impurities. It can be appreciated, however, that in general processing will be more efficient (and the catalyst more active) the lower the metal, nitrogen, and sulfur content of the feedstock.

Using SSZ-25 catalyst which contains a hydrogenation promoter, heavy petroleum residual feedstocks, cyclic stocks and other hydrocrackate charge stocks can be hydrocracked at hydrocracking conditions including a temperature in the range of from 175° C. to 485° C., molar ratios of hydrogen to hydrocarbon charge from 1 to 100, a pressure in the range of from 0.5 to 350 bar, and a liquid hourly space velocity (LHSV) in the range of form 0.1 to 30.

The hydrocracking catalysts contain an effective amount of at least one hydrogenation catalyst (component) of the type commonly employed in hydrocracking catalysts. The hydrogenation component is generally selected from the group of hydrogenation catalysts consisting of one or more metals of Group VIB and Group VIII, including the salts, complexes and solutions containing such. The hydrogenation catalyst is preferably selected from the group of metals, salts and complexes thereof of the group consisting of at least one of platinum, palladium, rhodium, iridium and mixtures thereof or the group consisting of at least one of nickel, molybdenum, cobalt, tungsten, titanium, chromium and mixtures thereof. Reference to the catalytically active metal or metals is intended to encompass such metal or metals in the elemental state or in some form such as an oxide, sulfide, halide, carboxylate and the like.

The hydrogenation catalyst is present in an effective amount to provide the hydrogenation function of the hydrocracking catalyst, and preferably in the range of from 0.05 to 25% by weight.

The catalyst may be employed in conjunction with traditional hydrocracking catalysts, e.g., any aluminosilicate heretofore employed as a component in hydrocracking catalysts. Representative of the zeolitic aluminosilicates disclosed heretofore as employable as component parts of hydrocracking catalysts are Zeolite Y (including steam stabilized, e.g., ultra-stable Y), Zeolite X, Zeolite beta (U.S. Pat. No. 3,308,069), Zeolite ZK-20 (U.S. Pat. No. 3,445,727), Zeolite ZSM-3 (U.S. Pat. No. 3,415,736), faujasite, LZ-10 (U.K. Patent 2,014,970, Jun. 9, 1982), ZSM-5-type zeolites, e.g., ZSM-5, ZSM-11, ZSM-12, ZSM-23, ZSM-35, ZSM-38, ZSM-48, crystalline silicates such as silicalite (U.S. Pat. No. 4,061,724), erionite, mordenite, offretite, chabazite, FU-1-type zeolite, NU-type zeolites, LZ-210-type zeolite and mixtures thereof. Traditional cracking catalysts containing amounts of $Na_2O$ less than about one percent by weight are generally preferred. The relative amounts of the SSZ-25 component and traditional hydrocracking component, if any, will depend at least in part, on the selected hydrocarbon feedstock and on the desired product distribution to be obtained therefrom, but in all instances an effective amount of SSZ-25 is employed. When a traditional hydrocracking catalyst (THC) component is employed, the relative weight ratio of the THC to the SSZ-25 is generally between about 1:10 and about 500:1, desirably between about 1:10 and about 200:1, preferably between about 1:2 and about 50:1, and most preferably is between about 1:1 and about 20:1.

The hydrocracking catalysts are typically employed with an inorganic oxide matrix component which may be any of the inorganic oxide matrix components which have been employed heretofore in the formulation of hydrocracking catalysts including: amorphous catalytic inorganic oxides, e.g., catalytically active silica-aluminas, clays, silicas, aluminas, silica-aluminas, silica-zirconias, silica-magnesias, alumina-borias, alumina-titanias and the like and mixtures thereof. The traditional hydrocracking catalyst and SSZ-25 may be mixed separately with the matrix component and then mixed or the THC component and SSZ-25 may be mixed and then formed with the matrix component.

SSZ-25 can be used to dewax hydrocarbonaceous feeds by selectively removing straight chain paraffins. The catalytic dewaxing conditions are dependent in large measure on the feed used and upon the desired pour point. Generally, the temperature will be between about 200° C. and about 475° C., preferably between about 250° C. and about 450° C. The pressure is typically between about 15 psig and about 3000 psig, preferably between about 200 psig and 3000 psig. The liquid hourly space velocity (LHSV) preferably will be from 0.1 to 20, preferably between about 0.2 and about 10.

Hydrogen is preferably present in the reaction zone during the catalytic dewaxing process. The hydrogen to feed ratio is typically between about 500 and about 30,000 SCF/bbl (standard cubic feet per barrel), preferably about 1000 to about 20,000 SCF/bbl. Generally, hydrogen will be separated from the product and recycled to the reaction zone. Typical feedstocks include light gas oil, heavy gas oils and reduced crudes boiling about 350° F.

The SSZ-25 hydrodewaxing catalyst may optionally contain a hydrogenation component of the type commonly employed in dewaxing catalysts. The hydrogenation component may be selected from the group of hydrogenation catalysts consisting of one or more metals of Group VIB and Group VIII, including the salts, complexes and solutions containing such metals. The preferred hydrogenation catalyst is at least one of the group of metals, salts and complexes selected from the group consisting of at least one of platinum, palladium, rhodium, iridium and mixtures thereof or at least one from the group consisting of nickel, molybdenum, cobalt, tungsten, titanium, chromium and mixtures thereof. Reference to the catalytically active metal or metals is intended to encompass such metal or metals in the elemental state or in some form such as an oxide, sulfide, halide, carboxylate and the like.

The hydrogenation component is present in an effective amount to provide an effective hydrodewaxing catalyst preferably in the range of from about 0.05 to 5% by weight.

SSZ-25 can be used to convert light straight run naphthas and similar mixtures to highly aromatic mixtures. Thus, normal and slightly branched chained hydrocarbons, preferably having a boiling range above about 40° C. and less than about 200° C., can be converted to products having a substantial aromatics content by contacting the hydrocarbon feed with the zeolite at a temperature in the range of from about 400° C. to 600° C., preferably 480° C.–550° C. at pressures ranging from atmospheric to 10 bar, and liquid hourly space velocities (LHSV) ranging from 0.1 to 15.

The conversion catalyst preferably contains a Group VIII metal compound to have sufficient activity for commercial use. By Group VIII metal compound as used herein is meant the metal itself or a compound thereof. The Group VIII noble metals and their compounds, platinum, palladium, and iridium, or combinations thereof can be used. The most preferred metal is platinum. The amount of Group VIII metal present in the conversion catalyst should be within the normal range of use in reforming catalysts, from about 0.05 to 2.0 weight percent, preferably 0.2 to 0.8 weight percent.

The zeolite/Group VIII metal conversion catalyst can be used without a binder or matrix. The preferred inorganic matrix, where one is used, is a silica-based binder such as Cab-O-Sil or Ludox. Other matrices such as magnesia and titania can be used. The preferred inorganic matrix is nonacidic.

It is critical to the selective production of aromatics in useful quantities that the conversion catalyst be substantially free of acidity, for example by poisoning the zeolite with a basic metal, e.g., alkali metal, compound. The zeolite is usually prepared from mixtures containing alkali metal hydroxides and thus have alkali metal contents of about 1–2 weight percent. These high levels of alkali metal, usually sodium or potassium, are unacceptable for most catalytic applications because they greatly deactivate the catalyst for cracking reactions. Usually, the alkali metal is removed to low levels by ion-exchange with hydrogen or ammonium ions. By alkali metal compound as used herein is meant elemental or ionic alkali metals or their basic compounds. Surprisingly, unless the zeolite itself is substantially free of acidity, the basic compound is required in the present process to direct the synthetic reactions to aromatics production.

The amount of alkali metal necessary to render the zeolite substantially free of acidity can be calculated using standard techniques based on the aluminum content of the zeolite. Under normal circumstances, the zeolite as prepared and without ion-exchange will contain sufficient alkali metal to neutralize the acidity of the catalyst. If a zeolite free of alkali metal is the starting material, alkali metal ions can be ion exchanged into the zeolite to substantially eliminate the acidity of the zeolite. An alkali metal content of about 100%, or greater, of the acid sites calculated on a molar basis is sufficient.

Where the basic metal content is less than 100% of the acid sites on a molar basis, the test described in U.S. Pat. No. 4,347,394 which patent is incorporated totally herein by reference, can be used to determine if the zeolite is substantially free of acidity.

The preferred alkali metals are sodium and potassium. The zeolite itself can be substantially free of acidity only at very high silica:alumina mole ratios; by "zeolite consisting essentially of silica" is meant a zeolite which is substantially free of acidity without base poisoning.

Hydrocarbon cracking stocks can be catalytically cracked in the absence of hydrogen using SSZ-25 at liquid hourly space velocities from 0.5 to 50, temperatures from about 260° F. to 1625° F. and pressures from subatmospheric to several hundred atmospheres, typically from about atmospheric to about 5 atmospheres.

For this purpose, the SSZ-25 catalyst can be composited with mixtures of inorganic oxide supports as well as traditional cracking catalyst.

The catalyst may be employed in conjunction with traditional cracking catalysts, e.g., any aluminosilicate heretofore employed as a component in cracking catalysts.

Representative of the zeolitic aluminosilicates disclosed heretofore as employable as component parts of cracking catalysts are Zeolite Y (including steam stabilized chemically modified, e.g., ultra-stable Y), Zeolite X, Zeolite beta (U.S. Pat. No. 3,308,069), Zeolite ZK-20 (U.S. Pat. No. 3,445,727), Zeolite ZSM-3 (U.S. Pat. No. 3,415,736), faujasite, LZ-10 (U.K. Patent 2,014,970, Jun. 9, 1982), ZSM-5-type zeolites, e.g., ZSM-5, ZSM-11, ZSM-12, ZSM-23, ZSM-35, ZSM-38, ZSM-48, crystalline silicates such as silicalite (U.S. Pat. No. 4,061,724), erionite, mordenite, offretite, chabazite, FU-1-type zeolite, NU-type zeolites, LZ-210-type zeolite and mixtures thereof. Traditional cracking catalysts containing amounts of $Na_2O$ less than about one percent by weight are generally preferred. The relative amounts of the SSZ-25 component and traditional cracking component, if any, will depend at least in part, on the selected hydrocarbon feedstock and on the desired product distribution to be obtained therefrom, but in all instances an effective amount of SSZ-25 is employed. When a traditional cracking catalyst (TC) component is employed, the relative weight ratio of the TC to the SSZ-25 is generally between about 1:10 and about 500:1, desirably between about 1:10 and about 200:1, preferably between about 1:2 and about 50:1, and most preferably is between about 1:1 and about 20:1.

The cracking catalysts are typically employed with an inorganic oxide matrix component which may be any of the inorganic oxide matrix components which have been employed heretofore in the formulation of FCC catalysts including: amorphous catalytic inorganic oxides, e.g., catalytically active silica-aluminas, clays, silicas, aluminas, silica-aluminas, silica-zirconias, silica-magnesias, alumina-borias, alumina-titanias and the like and mixtures thereof.

The traditional cracking component and SSZ-25 may be mixed separately with the matrix component and then mixed or the TC component and SSZ-25 may be mixed and then formed with the matrix component.

The mixture of a traditional cracking catalyst and SSZ-25 may be carried out in any manner which results in the coincident presence of such in contact with the crude oil feedstock under catalytic cracking conditions. For example, a catalyst may be employed containing the traditional cracking catalyst and a SSZ-25 in single catalyst particles or SSZ-25 with or without a matrix component may be added as a discrete component to a traditional cracking catalyst.

SSZ-25 is especially useful as a catalyst in a process for isomerizing one or more xylene isomers in a $C_8$ aromatic feed to obtain ortho-, meta- and para-xylene in a ratio approaching the equilibrium value. In particular, xylene isomerization is used in conjunction with a separation process to manufacture para-xylene. For example, a portion of the para-xylene in a mixed $C_8$ aromatics stream may be recovered by crystallization and centrifugation. The mother liquor from the crystallizer is then reacted under xylene isomerization conditions to restore ortho-, meta-, and para-xylenes to a near equilibrium ratio. At the same time, part of the ethylbenzene in the mother liquor is converted to xylenes or to products which are easily separated by distillation. The isomerate is blended with fresh feed and the combined stream is distilled to remove heavy and light by-products. The resultant $C_8$ aromatics stream is then sent to the crystallizer to repeat the cycle.

Xylene isomerization catalysts are judged on their ability to produce a near equilibrium mixture of xylenes and convert ethylbenzene with very little net loss of xylenes. The SSZ-25 type zeolites are especially effective in this regard. Accordingly, an additional aspect of the present invention is to provide a hydrocarbon conversion process which comprises contacting a $C_8$ aromatic stream of xylene ethylbenzene or mixture thereof, as well as a mixture of ethylbenzenes and other alkylbenzenes under isomerization conditions with a catalyst comprising SSZ-25.

The SSZ-25 may conveniently be used as an aggregate in the form of pellets or extrudates. An inorganic oxide binder such as gamma alumina or silica may be employed to provide attrition resistance.

In the vapor phase, suitable isomerization conditions include a temperature in the range 500°–1100° F., preferably 600°–1050° F., a pressure in the range 0.5–50 atm abs, preferably 1–5 atm abs, and a weight hourly space velocity (WHSV) of 0.1 to 100, preferably 0.5 to 50. Optionally, isomerization in the vapor phase is conducted in the presence of 3.0 to 30.0 moles of hydrogen per mole of alkylbenzene. If hydrogen is used, the catalyst should comprise 0.1 to 2.0 wt. % of a hydrogenation/dehydrogenation component selected from Group VIII of the Periodic Table, especially platinum or nickel. By Group VIII metal component is meant the metals and their compounds such as oxides and sulfides.

In the liquid phase, suitable isomerization conditions include a temperature in the range 100°–700° F., a pressure in the range 1–200 atm abs, and a WHSV in the range 0.5–50.

Optionally, the isomerization feed may contain 10 to 90 wt. % of a diluent such as toluene, trimethylbenzenes, naphthenes or paraffins.

SSZ-25 can also be used to oligomerize straight and branched chain olefins having from about 2 to 21 and preferably 2–5 carbon atoms. The oligomers which are the products of the process are medium to heavy olefins which are useful for both fuels, i.e., gasoline or a gasoline blending stock and chemicals.

The oligomerization process comprises contacting the olefin feedstock in the gaseous state phase with SSZ-25 at a temperature of from about 450° F. to about 1200° F., a WHSV of from about 0.2 to about 50 and a hydrocarbon partial pressure of from about 0.1 to about 50 atmospheres.

Also, temperatures below about 450° F. may be used to oligomerize the feedstock, when the feedstock is in the liquid phase when contacting the zeolite catalyst. Thus, when the olefin feedstock contacts the zeolite catalyst in the liquid phase, temperatures of from about 50° F. to about 450° F., and preferably from 80° to 400° F. may be used and a WHSV of from about 0.05 to 20 and preferably 0.1 to 10. It will be appreciated that the pressures employed must be sufficient to maintain the system in the liquid phase. As is known in the art, the pressure will be a function of the number of carbon atoms of the feed olefin and the temperature. Suitable pressures include from about 0 psig to about 3000 psig.

The zeolite can have the original cations associated therewith replaced by a wide variety of other cations according to techniques well known in the art. Typical cations would include hydrogen, ammonium and metal cations including mixtures of the same. Of the replacing metallic cations, particular preference is given to cations of metals such as rare earth metals, manganese, calcium, as well as metals of Group II of the Periodic Table, e.g., zinc, and Group VIII of the Periodic Table, e.g., nickel. One of the prime requisites is that the zeolite have a fairly low aromatization activity, i.e., in which the amount of aromatics produced is not more than about 20% by weight. This is accomplished by using a zeolite with controlled acid activity [alpha value] of from about 0.1 to about 120, preferably from about 0.1 to about 100, as measured by its ability to crack n-hexane.

Alpha value are defined by a standard test known in the art, e.g., as shown in U.S. Pat. No. 3,960,978 which is incorporated totally herein by reference. If required, such zeolites may be obtained by steaming, by use in a conversion process or by any other method which may occur to one skilled in this art.

SSZ-25 can be used to convert light gas $C_2$–$C_6$ paraffins and/or olefins to higher molecular weight hydrocarbons including aromatic compounds. Operating temperatures of 100° C.–700° C., operating pressures of 0 to 1000 psig and space velocities of 0.5–40 hr$^{-1}$ WHSV (weight hourly space velocity) can be used to convert the $C_2$–$C_6$ paraffin and/or olefins to aromatic compounds. Preferably, the zeolite will contain a catalyst metal or metal oxide wherein said metal is selected from the group consisting of Group IB, IIB, VIII and IIIA of the Periodic Table, and most preferably gallium and in the range of from about 0.05 to 5% by weight.

SSZ-25 can be used to condense lower aliphatic alcohols having 1 to 8 carbon atoms to a gasoline boiling point hydrocarbon product comprising mixed aliphatic and aromatic hydrocarbon. The condensation reaction proceeds at a temperature of about 500° F. to 1000° F., a pressure of about 0.5 to 1000 psig and a space velocity of about 0.5 to 50 WHSV. The process disclosed in U.S. Pat. No. 3,984,107 more specifically describes the process conditions used in this process, which patent is incorporated totally herein by reference.

The catalyst may be in the hydrogen form or may be base exchanged or impregnated to contain ammonium or a metal cation complement, preferably in the range of from about 0.05 to 5% by weight. The metal cations that may be present include any of the metals of the Groups I through VIII of the Periodic Table. However, in the case of Group IA metals, the cation content should in no case be so large as to effectively inactivate the catalyst.

The conversion of hydrocarbonaceous feeds can take place in any convenient mode, for example, in fluidized bed, moving bed, or fixed bed reactors depending on the types of process desired. The formulation of the catalyst particles will vary depending on the conversion process and method of operation.

Other reactions which can be performed using the catalyst of this invention containing a metal, e.g., platinum, include hydrogenation-dehydrogenation reactions, denitrogenation and desulfurization reactions.

SSZ-25 can be used in hydrocarbon conversion reactions with active or inactive supports, with organic or inorganic binders, and with and without added metals. These reactions are well known to the art, as are the reaction conditions.

SSZ-25 can also be used as an adsorbent, as a filler in paper, paint, and toothpastes, and as a water-softening agent in detergents.

The following Examples illustrate the preparation of SSZ-25.

EXAMPLES

Example 1

Preparation of N,N,N-Trimethyl-1-adamantanammonium Hydroxide (Template A)

Ten (10) grams of 1-adamantanamine (Aldrich) was dissolved in a mixture of 29 gms tributylamine and 60 mls dimethylformamide. The mixture was chilled in an ice bath.

28.4 Grams of methyl iodide were added dropwise to the chilled solution with continuous stirring. After several hours, crystals appear. The reaction was continued overnight and allowed to come to room temperature. The crystals were filtered and washed with tetrahydrofuran and then diethyl ether before vacuum drying. Additional product was obtained by adding enough diethyl ether to the reaction filtrate to produce two phases and then with vigorous stirring acetone was added until the solution just became one phase. Continued stirring produced crystallization at which time the solution can be chilled to induce further Crystallization. The product has a melting point near 300° C. (decomp.) and the elemental analyses and NMR are consistent with the known structure. The vacuum-dried iodide salt was then ion-exchanged with ion-exchange resin AG 1×8 (in molar excess) to the hydroxide form. The exchange was performed over a column or more preferably by overnight stirring of the resin beads and the iodide salt in an aqueous solution designed to give about a 0.5 molar solution of the organic hydroxide. This produces Template A.

Example 2

Preparation of N,N,N-Trimethyl-2-adamantanammonium Hydroxide (Template B)

Five grams of 2-adamantanone (Aldrich Chemical Co.) was mixed with 2.63 gms of formic acid (88%) and 4.5 gms of dimethyl formamide. The mixture was then heated in a pressure vessel for 16 hours at 190° C. Care should be taken to anticipate the increase in pressure the reaction experiences due to $CO_2$ evolution. The reaction was conveniently carried out in a Parr 4748 reactor with teflon liner. The workup consists of extracting N,N dimethyl-2-adamantamine from a basic (pH=12) aqueous solution with diethyl ether. The various extracts were dried with $Na_2SO_4$, the solvent removed and the product taken up in ethyl acetate. An excess of methyl iodide was added to a cooled solution which was then stirred at room temperature for several days. The crystals were collected and washed with diethyl ether to give N,N,N trimethyl-2-adamantammonium iodide. The product is checked by microanalysis for C, H, and N. The conversion to the hydroxide form was carried out analogously to Template A above.

Example 3

4.5 Grams of a 0.67M solution of Template B in its hydroxide form were mixed with 6 ml $H_2O$ and 0.103 gms of KOH (solid). After dissolution, 2.36 gms of Ludox AS-30 colloidal silica (30% $SiO_2$) were added with stirring using a magnetic stir bar. Finally, 0.78 gms of Nalco 1SJ612 alumina on silica (30% solids, 4% $Al_2O_3$ overall) was added. The reactants were loaded into a Parr 4745 reactor, sealed and loaded onto a rotating spit in a Blue M oven. The reactor was rotated at 30 RPM while being heated at 175° C. for 10 days. The product after filtration, washing with distilled water, drying in air and then at 100° C. was the crystalline material designated SSZ-25. The X-ray diffraction pattern of the as-made material is tabulated in Table 4 below.

TABLE 4

| 2 Θ | d/n | I/I$_o$ |
|---|---|---|
| 3.05 | 29.0 | 20 |
| 6.42 | 13.77 | 100 |
| 7.18 | 12.31 | 100 |
| 7.88 | 11.22 | 47 |
| 9.62 | 9.19 | 53 |
| 12.85 | 6.89 | 13 |
| 14.37 | 6.16 | 10 |
| 14.73 | 6.01 | 23 |
| 15.75 | 5.63 | 27 |
| 16.13 | 5.49 | 13 |
| 19.37 | 4.58 | 47 |
| 20.09 | 4.42 | 23 |
| 20.78 | 4.27 | 10 |
| 21.65 | 4.105 | 50 |
| 22.57 | 3.939 | 50 |
| 23.05 | 3.858 | 30 |
| 23.70 | 3.754 | 17 |
| 25.00 | 3.562 | 20 |
| 26.03 | 3.423 | 73 |
| 26.85 | 3.320 | 33 |
| 27.28 | 3.269 | 17 |
| 28.91 | 3.088 | 13 |

Example 4

6.02 Grams of a 0.71M solution of Template A were mixed with 0.14 gms KOH(s), 0.088 gms of Reheis F-2000 hydrated alumina, and 8 ml $H_2O$. After thorough mixing, 4.0 gms of Ludox AS-30 was blended in as silica source. The reaction mixture was heated in the teflon cup of a Parr 4745 reactor at 175° C. at 435 RPM for 7 days. Workup as in Example 3 produced crystalline SSZ-25.

Example 5

In this example, the same reactants were used as in Example 4 but the initial $SiO_2/Al_2O_3$ ratio was increased to 75. 0.051 of Reheis F-2000 hydrated alumina was used and dissolved in the same quantity KOH, 6.4 gms of the same Template A solution and 6.8 ml H$_2$O. The same quantity of Ludox was used and the reaction was again run at 175° C. but at 30 RPM. At 7 days of reaction, the product was largely amorphous but by 10 days of reaction the product was crystalline SSZ-25. The SiO$_2$/Al$_2$O$_3$ value of the zeolite is 75.

Example 6

3.00 Grams of a 1.04M solution of Template A was mixed with 9 ml of H$_2$O, 0.195 gms of KOH(s), 0.083 gms of Reheis F-2000 hydrated alumina, and finally 0.90 gms of Cabosil M5. The mixture was heated at 175° C. for 7 days without agitation. The crystalline product was SSZ-25 and has a SiO$_2$/Al$_2$O$_3$ ratio of 30.

Example 7

A reaction like Example 4 was set up again. This time a half-inch diameter teflon ball was added to the reactor to aid in mixing during the tumbling of the reactor. The crystalline product after 7 days of reaction and the usual workup was SSZ-25.

Example 8

The crystalline products of Examples 3–7 were subjected to calcination as follows. The samples were heated in a muffler furnace from room temperature up to 540° C. at a steadily increasing rate over a 7-hour period. The samples were maintained at 540° C. for four more hours and then taken up to 600° C. for an additional four hours. A 50/50 mixture of air and nitrogen was passed over the zeolites at a rate of 20 standard cubic feet per minute during heating.

Representative X-ray diffraction data for the calcined products of Example 3 appears in Table 5.

TABLE 5

| 2 Θ | d/n | I/I$_o$ |
|---|---|---|
| 3.35 | 26.4 | 18 |
| 7.18 | 12.31 | 100 |
| 8.00 | 11.05 | 62 |
| 10.04 | 8.80 | 68 |
| 12.90 | 6.86 | 12 |
| 14.33 | 6.18 | 44 |
| 14.80 | 5.99 | 12 |
| 16.01 | 5.53 | 18 |
| 20.31 | 4.37 | 18 |
| 21.70 | 4.10 | 44 |
| 22.73 | 3.91 | 41 |
| 23.80 | 3.74 | 24 |
| 25.02 | 3.559 | 15 |
| 26.06 | 3.420 | 68 |
| 27.02 | 3.300 | 15 |
| 27.89 | 3.999 | 18 |
| 28.71 | 3.109 | 12 |

The SSZ-25 product of Example 4 was also calcined in a muffler furnace at 463° C. for a period of 2 hours and the representative X-ray diffraction data for the calcined product appears in Table 6 below.

TABLE 6

| 2 Θ | d/n | I/I$_o$ |
|---|---|---|
| 3.5 | 25.2 | 16 |
| 7.20 | 12.28 | 110 |
| 8.07 | 10.96 | 47 |
| 9.68 | 9.14 | 74 |

TABLE 6-continued

| 2 Θ | d/n | I/I$_o$ |
|---|---|---|
| 10.08 | 8.77 | 58 |
| 13.05 | 6.78 | 15 |
| 14.37 | 6.16 | 36 |
| 14.82 | 5.98 | 11 |
| 16.10 | 5.50 | 16 |
| 18.03 | 4.92 | 8 |
| 20.30 | 4.37 | 12 |
| 20.95 | 4.24 | 18 |
| 21.66 | 4.10 | 11 |
| 21.97 | 4.05 | 18 |
| 22.80 | 3.900 | 34 |
| 23.80 | 3.739 | 18 |
| 25.03 | 3.558 | 14 |
| 25.32 | 3.517 | 15 |
| 26.10 | 3.414 | 61 |
| 27.05 | 3.296 | 15 |
| 27.95 | 3.192 | 14 |
| 28.71 | 3.109 | 11 |

Considerable changes in peak position and intensity can be observed in comparing the data for SSZ-25 before and after calcination.

Example 9

Ion-exchange of the calcined SSZ-25 materials from Example 18 was carried out using NH$_4$NO$_3$ to convert the zeolites from their K form to NH$_4$ and then eventually H form. Typically the same mass of NH$_4$NO$_3$ as zeolite was slurried into H$_2$O at ratio of 50/1 H$_2$O to zeolite. The exchange solution was heated at 100° C. for two hours and then filtered. This process was reported four times. Finally, after the last exchange the zeolite was washed several times with H$_2$O and dried. A repeat calcination as in Example 8 was carried out but without the final treatment at 600° C. This produces the H form of SSZ-25 zeolite.

Example 10

The product of Example 6, after sequential treatment as in Examples 8 and then 9, was subjected to a surface area and pore size distribution analysis using N$_2$ as adsorbate and via the BET method. The surface area of the zeolitic material was 520 m$^2$/gm and the micropore volume was 0.18 cc/gm.

Example 11

Constraint Index Determination 0.25 Grams of the hydrogen form of the zeolite of Example 3 (after treatment according to Examples 8 and 9, was packed into a ⅜" stainless steel tube with alundum on both sides of the zeolite bed. A Lindberg furnace was used to heat the reactor tube. Helium was introduced into the reactor tube at 10 cc/min. and atmospheric pressure. The reactor was taken to 250° F. for 40 min. and then raised to 600° F. Once temperature equilibration was achieved, a 50/50, w/w feed of n-hexane and 3-methylpentane was introduced into the reactor at a rate of 0.62 cc/hr. Feed delivery was made via syringe pump. Direct sampling onto a gas chromatograph begun after 10 minutes of feed introduction. The constraint index value was calculated from gas chromatographic data using methods known in the art.

| Example No. | C.I. | Conversion at 10 min. | Temp. °F. |
|---|---|---|---|
| 3 | 0.3 | 65% | 600 |

Example 12

The following example illustrates the use of SSZ-25 as a reforming catalyst. The hydrogen form of SSZ-25 was prepared as in Ex. 9. The catalyst was then back-exchanged at pH=10 with KOH at 80° C. After calcination at 1000° F., the catalyst showed no cracking activity at 800° F. The catalyst was impregnated with an aqueous solution of platinum tetramine dinitrate to give a platinum loading of 0.8%. After calcination, the screening test was run on a light paraffinic $C_5$–$C_7$ straight run feed as follows:

LHSV=6
$H_2$/HC=6
Psig=100
Temp.=860

After several hours on stream, the catalyst showed about 40% conversion of the $C_6$ and $C_7$ paraffins with a 35% selectivity to aromatics consisting chiefly of benzene, toluene and xylenes.

Example 13

The acid form of SSZ-25 was prepared as in Ex. 9 and tested for the conversion of methanol to liquid products. 0.5 gm of catalyst was loaded into a ⅜" stainless steel reactor tube which was heated in a Lindberg furnace to 1000° F. The temperature was reduced to 700° F. in a stream of helium at 20 cc/min. Methanol was introduced into the reactor at a rate of 1.25 cc/hr. The conversion at 10 minutes was close to 100% and dropped only slightly over several hours. The product distribution is given in Table 7 below.

TABLE 7

| Conversion of Methanol over SSZ-25 zeolite (at 85 min.) | |
|---|---|
| Product | wt. % |
| Methane | 0.4 |
| Ethylene | 1.1 |
| Ethane | 0.0 |
| Propylene | 3.2 |
| Propane | 2.2 |
| Methanol | 0.0 |
| Dimethyl Ether | 0.0 |
| $C_4$ | 10.3 |
| $C_5$ | 6.8 |
| $C_6$ (non-aromatic) | 7.2 |
| Benzene | 0.0 |
| Toluene | 5.8 |
| p,m Xylene | 13.1 |
| o, Xylene | 4.7 |
| $C_6+$ | 38.5 |

As can be seen in the table, the SSZ-25 makes very little light gas and produces considerable liquid product under these conditions.

Example 14

When the hydrogen form of SSZ-25 is ion-exchanged with $Ga_2(SO_4)_3$ at reflux for several hours and then calcined, a catalyst is produced which is capable of aromatization under cracking conditions. When the constraint index test was run as in Example 11 but at 800° F., the conversion was greater than 70% with greater than 50% of the product as aromatics.

Example 15

The same catalyst as in Example 14 is tested for aromatization of n-butane at 940° F. The feed is 2% n-butane in helium run at atmospheric pressure. As the space rate is adjusted, for conversions of about 45% and greater, the yield of aromatics is 45–50% demonstrating the ability of the gallium exchanged SSZ-25 to convert light gases to aromatics.

Example 16

The hydrogen form of the SSZ-25 zeolite may also be advantageously used in the isomerization of xylenes and conversion of ethylbenzene. The hydrogen form of the SSZ-25 zeolite was tested as catalyst for xylene isomerization. A portion of the HSSZ-25 powder from Example 9 was pelleted, crushed and sieved to obtain 20–40 mesh granules, which were then calcined for four hours at 1000° F. One gram of the calcined material was charged to a ³⁄₁₆-inch I.D. tubular microreactor heated by an electric furnace. The catalyst bed was heated to 750° F. in flowing helium. The helium was then replaced with a mixed xylene feed. The feed composition and reactor effluent were analyzed by gas chromatography. The test results are shown in Table 8. The HSSZ-25 catalyst produced a near equilibrium mixture of xylene isomers with excellent ethylbenzene conversion and very little xylene loss.

TABLE 8

| Xylene Isomerization Over HSSZ-25 | | |
|---|---|---|
| Hours on Stream | 8–23 | |
| Temperature, °F. | 750 | |
| WHSV | 5 | |
| Pressure, psig | 23 | |
| Composition, wt % | Feed | Product |
| non-aromatics | 0.44 | 1.05 |
| benzene | 0.00 | 1.99 |
| toluene | 1.34 | 3.69 |
| ethylbenzene | 9.76 | 6.37 |
| p-xylene | 9.61 | 19.37 |
| m-xylene | 53.99 | 43.06 |
| o-xylene | 23.10 | 20.00 |
| heavy aromatics | 1.77 | 4.46 |
| Percent EB conversion | | 34.7 |
| Percent xylene loss | | 4.3 |
| p-xyl % approach to equil. | | 99.6 |

Example 17

The hydrogen form of SSZ-25 can be used in catalytic cracking. For such purposes, the catalyst prepared as in Ex. 9 was tested in a micro-activity test (MAT) using the procedure developed by ASTM Committee D-32. The test was run at 925° F. on fresh catalyst at a cat/oil ratio of 3 (based upon catalyst calcined to 1100° F.) and a WHSV of 15–16. Table 9 shows inspections on the feed and the resulting products. The catalyst was run at 20 wt. % in a kaolin matrix.

TABLE 9

MAT Test for SSZ-25 Zeolite

| FEED | |
|---|---|
| API | 29.09 |
| Aniline pt, °F. | 219.1 |
| Ramsbottom Carbon, wt. % | 0.3 |
| N(T), ppm | 270 |
| N(B), ppm | 159 |
| S(T), wt. % | 0.54 |
| TEST DATA | |
| Conversion, wt % | 55.2 |
| Coke, wt. % | 4.7 |
| $C_5$— 430° F. | 22.0 |
| 430–650° F. | 19.0 |
| 650+ | 26.0 |
| $C_3$— | 13.6 |
| $C_4$— | 28.5 |
| $C_4$ olefin/$C_4$ total | 0.46 |

Example 18

The hydrogen form of SSZ-25 as prepared in Ex. 9 can also be used as a dewaxing catalyst selectively removing n-paraffins from waxy feeds. The dewaxing catalyst is prepared as an extrudate with platinum on the zeolite. The zeolite comprises only 5% of the extrudate, the remainder being Catapal alumina. The platinum loading on the zeolite was 1%. 2.5 gms of hydrogen SSZ-25 are added to a blend of 33.93 gms of Catapal alumina (70% $Al_2O_3$) and 34.62 gms of Kaiser alumina (68.6% $Al_2O_3$). 20 cc of 10% $HNO_3$ are added slowly with mixing and then another 30 cc $H_2O$ are added to give a dough-like consistency. The bound zeolite is dried overnight under partial vacuum at 120° C. Calcination is carried out at 450° F. for 1 hour, followed by 1000° F. for an hour.

30 ml of methanol are added to 12 gms of the calcined extrudate. 0.26 gms of platinum tetramine dinitrate in 24 cc $H_2O$ is added to the methanol/catalyst slurry. The mixture is tumbled while under vacuum and at 110° C. to slowly remove the co-solvent system over a 1.25 hr. period. After drying overnight at 120° C. and partial vacuum, the catalyst is calcined at 450° F. for 2 hrs. and 900° F. for 1 hr.

6.2 cc of catalyst (24–48 mesh) were loaded into a ⅜" reactor tube which was placed in a furnace. The catalyst was dried at 400° F. under nitrogen (1000 psi) for an hour. The temperature was reduced to 300° F., the gas inlet was switched to hydrogen (2150 psi) and the catalyst bed was brought to 650° F. in 25 deg./half-hour increments.

Table 10 shows the characteristics of the waxy, hydrocracked Alaskan North Slope Medium Neutral VGO feed. Also shown is data for pour point reduction as a function of temperature using the catalyst prepared above.

TABLE 10

Use of SSZ-25 in Pour Point Reduction of Waxy Lube Stock

| FEED | |
|---|---|
| API | 34.0 |
| Aniline pt, °F. | 244.0 |
| Sulfur, ug/ul | 0.34 |
| Nitrogen, ug/ul | 0.11 |
| Pour Point | 100° F. |
| Paraffin content | 25% |
| | (by mass spec.) |
| Naphthenes | 62% |
| Aromatics | 13% |

TABLE 10-continued

Use of SSZ-25 in Pour Point Reduction of Waxy Lube Stock

| PRODUCT | | |
|---|---|---|
| Run temp. | 600 | 660(*) |
| Lube Yield | 72% | 69% |
| Pour Point | 20° F. | 10° F. |
| Cloud Point | 32° F. | 40° F. |
| V.I. (corrected) | 110 | 108 |

*feed spiked with quinoline to give 3 ppm $NH_3$ level in the $H_2$ once through gas.

Example 19

The hydrogen form of the SSZ-25 zeolite can be used in hydrocracking conversions of hydrocarbon feeds. The data shown in Table 11 is for the conversion of a feed made up of representative model compounds. The data illustrates the high activity and shape-selectivity for SSZ-25 zeolite in hydroprocessing. The catalyst is active by itself or when a noble metal is incorporated. One gram (dry basis) of catalyst was loaded into a ¼" reactor tube packed with alundum on either side of the bed. The catalyst was dried at 500° F. for 30 min. with 1200 psi $H_2$. The hydrogen flow rate is 55 cc/min. at atmospheric pressure and room temperature. The feed rate was 50 microliters/min. and the catalyst was equilibrated for 2 hours at temperature before G.C. analysis.

TABLE 11

Hydroprocessing of a Model Feed with SSZ-25 Zeolite

| CATALYST | FEED ALONE | SSZ-25 | SSZ-25 (0.5% Pd) |
|---|---|---|---|
| TEMP. | — | 700° F. | 500° F. |
| LHSV | | | |
| $H_2$ PRESSURE | | 1200 | 1200 |
| CONVERSION | | 49% | 46% |
| PRODUCT/FEED wt. % | | | |
| $C_1$–$C_6$ | 0.0 | 44.8 | 13% |
| 2,2-dimethylbutane Marker | 0.99 | 0.90 | 0.95 |
| Cyclohexane | 30.8 | 0.43 | 30.2 |
| Isooctane(2,2,4) | 4.4 | 4.0 | 4.6 |
| Methylcyclohexane | 0.0 | 0.0 | 23.9 |
| Toluene | 30.8 | 21.7 | 0.0 |
| 3,4,Diethyl $C_6$ | 5.5 | 5.3 | 4.6 |
| 4-Propyl heptane | 5.5 | 9.5 | 4.2 |
| n-Decane | 5.6 | 0.75 | 1.3 |
| t-Decalin | 6.2 | 6.7 | 7.1 |
| c-Decalin | 4.7 | 1.2 | 0.6 |
| n-Dodecane | 5.6 | 0.0 | 0.6 |

As can be seen above, the catalyst has surprising selectivity for n-paraffins and a selectivity for cis decalin over the trans isomer. The reactivity is also somewhat pressure dependent.

What is claimed is:

1. A hydrocarbon conversion process comprising using calcined SSZ-25 zeolite under hydrocarbon conversion conditions in the reaction of alkylating aliphatics wherein said zeolite has the X-ray diffraction lines of Table 2.

2. A hydrocarbon conversion process comprising using calcined SSZ-25 zeolite under hydrocarbon conversion conditions in the reaction of alkylating aromatics wherein said zeolite has the X-ray diffraction lines of Table 2.

3. The process according to claim 2, wherein the aromatics being alkylated include benzene.

4. The process according to claim 2, wherein the alkylating reaction produces higher alkyl benzenes.

* * * * *